United States Patent [19]

Tolle et al.

[11] Patent Number: 5,212,287
[45] Date of Patent: May 18, 1993

[54] PENTAPEPTIDE SYNTHESIS

[75] Inventors: John C. Tolle, Zion; Wenying Z. Gifford, Vernon Hills; Kenneth W. Funk, Lindenhurst, all of Ill.

[73] Assignee: Immunetech Pharmaceuticals, Inc., San Diego, Calif.

[21] Appl. No.: 287,865

[22] Filed: Dec. 21, 1988

[51] Int. Cl.$^5$ ............................................. C07C 103/52
[52] U.S. Cl. .................................. 530/330; 530/331; 530/335; 548/532
[58] Field of Search ........................ 530/330, 331, 335

[56] References Cited

U.S. PATENT DOCUMENTS 4,161,522  7/1979  Hamburger .......................... 424/177
4,171,299  10/1979  Hamburger .................. 260/112.5 R

OTHER PUBLICATIONS

S. Guttmann, Helv. Chim. Acta 44, pp. 721–744 (1961).
D. Laufer & E. Blout, JACS 89, pp. 1246–1249 (1967).

*Primary Examiner*—David B. Springer
*Attorney, Agent, or Firm*—Lyon & Lyon

[57] ABSTRACT

A method of synthesizing commercial quantities of the pentapeptide L-aspartyl-L-seryl-L-aspartyl-L-prolyl-L-arginine, and salts or solvates thereof, e.g., the hydrochloride or acetate salt or water solvate, compounds useful in pharmaceutical compositions for the treatment of allergic conditions, is disclosed, as are novel intermediate compounds produced in the course of the synthesis.

11 Claims, No Drawings

PENTAPEPTIDE SYNTHESIS

FIELD OF THE INVENTION

This invention relates to a synthesis of commercial quantities of the pentapeptide L-aspartyl-L-seryl-L-aspartyl-L-prolyl-L-arginine. This pentapeptide, abbreviated Asp-Ser-Asp-Pro-Arg, can be represented by the structural formula:

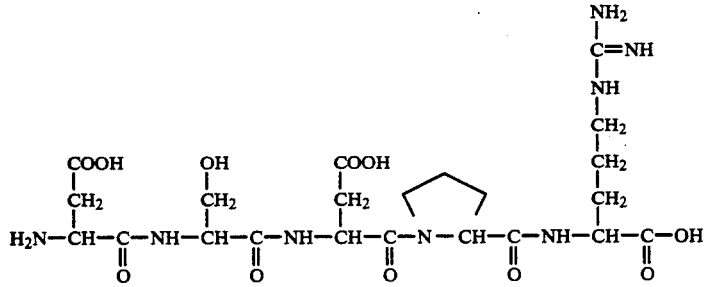

and the empirical formula $C_{22}H_{36}N_8O_{11}$. The pentapeptide can be recovered from the synthesis as the free base or in various salt or solvate forms, e.g., as the hydrochloride or acetate salt or water solvate.

Asp-Ser-Asp-Pro-Arg is one of a family of peptides known to be useful in reducing or preventing an allergic reaction. See U.S. Pat. Nos. 4,161,522 and 4,171,299, issued Jul. 17 and Oct. 16, 1979, respectively, to Hamburger.

This invention further relates to novel intermediate compounds produced in the course of the synthesis of Asp-Ser-Asp-Pro-Arg by the method of the invention.

BACKGROUND OF THE INVENTION

To the uninitiated, the synthesis of peptides may seem to be relatively straightforward. A free carboxyl group in an amino acid, conventionally one having its other reactive group or groups, such as the amino functionality, protected with a removable reaction-blocking group, is coupled to a free amino group in another amino acid whose other reactive groups, including its carboxyl group, are also protected with different reaction-blocking groups. After removing a protecting group from a carboxyl or an amino group in the thus-coupled amino acids, one can then seek to couple an additional amino acid having a protected carboxyl and an unprotected amino group, or vice versa, to the starting amino acid pair, and in theory this can be repeated as often as necessary to increase the length of the peptide chain and give the desired peptide.

The amino acids used are known, as are typical protecting group-providing reagents, coupling agents, activating agents and other materials used in conventional liquid state and solid state peptide syntheses. The latter syntheses involve first attaching an amino acid to a solid support and then building the peptide chain outward from this first, immobilized reactant. Materials and methods for use in the purification procedures which must be practiced to give usable intermediate and final products from such syntheses are also known. Hence, one might suppose that all that is needed to synthesize a peptide is, first of all, paper and pencil with which to draw the desired amino acid sequence, and then the known materials to subject to the known procedures.

In peptide synthesis, however, as in other fields of human endeavor, it is all too often the case that art does not imitate life. Despite all that is known, synthesizing significant amounts of peptides at a cost that permits their use in affordable pharmaceutical compositions is oftentimes extraordinarily difficult. And this has been found to be especially true in the case of Asp-Ser-Asp-Pro-Arg.

SUMMARY OF THE INVENTION

This invention provides a method of synthesizing commercial quantities of Asp-Ser-Asp-Pro-Arg at acceptably low cost. This method involves:

liquid phase synthesis of intermediates and final products;

purification of intermediates and final products by precipitation, trituration, crystallization, recrystallization and chromatographic techniques;

the use of mixtures of protected and unprotected amino acid-containing intermediates to give the desired peptide intermediates and final products in acceptable yields.

This method can be represented by the following illustrative equations in which the abbreviations used have the following meanings:

| Abbreviation | Meaning |
|---|---|
| Asp | L-Aspartic acid |
| Ser | L-Serine |
| Pro | L-Proline |
| Arg | L-Arginine |
| Z | Carbobenzoxy |
| Bzl | Benzyl |
| DCC | Dicyclohexylcarbodiimide |
| HONP | p-Nitrophenol |
| Boc | t-Butyloxycarbonyl |
| HOSu | N-Hydroxysuccinimide |
| HOBt | Hydroxybenzotriazole |
| DIEA | Diisopropylethylamine |

I. PREPARATION OF ASP—PRO—ARG:

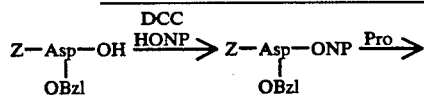

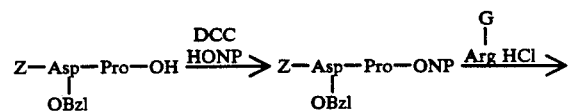

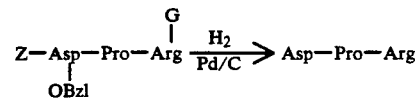

II. PREPARATION OF ASP—SER—ASP—PRO—ARG:

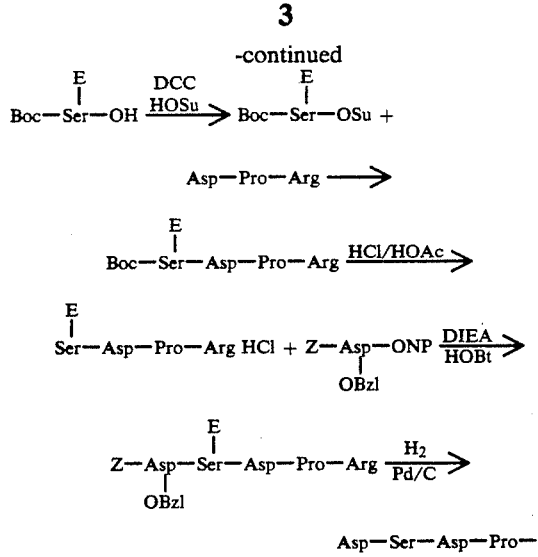

In these formulas E represents the hydroxyl-containing side chain of serine unprotected or bearing a hydroxyl protecting group, e.g., a benzyl ether-protected side chain; G represents the arginine side chain having its terminal amino group unprotected or protected, e.g., as the nitroarginine derivative, from which the nitro group can be removed by catalytic hydrogenation.

It is, therefore, an object of this invention to provide a synthesis of Asp-Ser-Asp-Pro-Arg and its salts and solvates.

It is also an object of this invention to provide a liquid phase method of synthesizing commercial quantities of Asp-Ser-Asp-Pro-Arg, its salts and solvates, at acceptably low cost.

A further object of this invention is to provide a liquid phase synthesis of Asp-Ser-Asp-Pro-Arg and its salts and solvates that employs mixtures of protected and unprotected amino acid-containing intermediates to give acceptable yields of the desired peptide intermediates and final products in acceptably pure form.

Another object of this invention is to provide novel intermediate compounds useful in the synthesis of Asp-Ser-Asp-Pro-Arg and its salts and solvates.

These and other objects, as well as the nature, scope and utilization of this invention, will become readily apparent to those skilled in the art from the following description and the appended claims.

DETAILED DESCRIPTION OF THE INVENTION

In carrying out the two reaction scheme illustrated, in general:

1. Depending on the coupling conditions and the amino acid or peptide components involved in the particular reaction step, protecting groups other than the carbobenzoxy, benzyl and t-butyloxycarbonyl groups shown can also be used. These include other carboxyl protecting groups such as substituted or unsubstituted aliphatic ester protecting groups such as methyl, ethyl, 2,2,2-trichloroethyl and t-butyl esters; other aralkyl ester protecting groups such as p-nitrobenzyl, p-methoxybenzyl, diphenylmethyl and triphenylmethyl(-trityl) esters; N-substituted hydrazides such as t-butyloxycarbonylhydrazides and carbobenzyloxycarbonylhydrazides; other amine protecting groups such as sulfonyl protecting groups, e.g., berzensulfonyl, toluenesulfonyl(tosyl), o-nitrophenylsulfenyl, tritylsulfenyl, and the like; acyl protecting groups, e.g., formyl, trifluoroacetyl, phthalyl, o-nitrophenoxyacetyl, chloroacetyl, acetyl, γ-chlorobutyryl, and the like; aromatic urethane protecting groups, e.g., benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 2-(p-biphenyl)isopropyloxycarbonyl and 2-benzoyl-1-methylvinyl; and the like. See, for example, Schroder et al, "The Peptides", Vol. 1 (Academic Press, 1965) at pages 181-207, Merrifield, *Adv. Enzym.*, 32, 221 (1969), and the aforementioned Hamburger patents. In every case, however, the protecting group will be one that:

gives crystallizable or amorphous solid intermediates, and if present in the precursors of Asp-Pro-Arg or in the intermediate whose deprotection gives Asp-Ser-Asp-Pro-Arg, is removable by acid treatment, or preferably by catalytic hydrogenation.

2. Other conventional coupling agents besides DCC, including other carbodiimides such as diisopropylcarbodiimide, azides such as diphenylphosphorylazide (DPPA), dicarboximides such as N-hydroxy-5-norbornene-2,3-dicarboximide and alkyl chloroformates such as ethylchloroformate or isobutylchloroformate, acid chlorides such as thionyl chloride, N-protected amino acids activated by the formation of a suitable ester, e.g., substituted phenyl esters, alkyl or aryl thioesters, substituted 8-hydroxyisoquinoline esters and 2-thiopyridyl esters, cyanidates such as diethylphosphorocyanidate, benzotriazol-1-yloxytris(dimethylamino)phosphonium hexafluorophosphate, bis(2-oxo-3-oxazolidinyl)phosphinic chloride, and the like, can be used, as can other activating agents besides 1-hydroxybenzotriazole, such as ethyl 2-hydroximino-2-cyanoacetate, 3-hydroxy-3,4-dihydro-1,2,3-benzotriazin-4-one, and the like.

3. The reactions to form carboxyl-activated esters and the coupling reactions preferably will be carried out at temperatures below those at which either racemization or side reactions, for example the reaction of the Asp side chain with the Ser side chain or the reaction of the Asp side chain with α-Asp-Ser amide, will occur to any significant extent. Ordinarily, to accomplish these desirable results the temperatures at which these reactions are carried out will be less than about 30° C., with temperatures ranging from about −5° to about 30° C. being preferred. Following the completion of an activation, esterification or coupling reaction, during purification or other work-up, the temperature can be raised as necessary so long as it remains less than about 40° C.

4. The activation, esterification and coupling reactions preferably will be carried out at a slightly acidic, neutral or slightly alkaline pH, i.e., one at which racemization, side reactions or saponification of protecting groups such as the benzyl group will not occur to any significant extent. An alkaline pH ranging from slightly above 7 to about 8 is preferred, and is preferably obtained and maintained using a tertiary amine, e.g., a trialkylamine such as triethylamine, tripropylamine or diisopropylethylamine, an N-alkylmorpholine such as N-methylmorpholine, and the like.

I. PREPARATION OF ASP-PRO-ARG

A. Preparation of

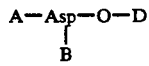

(A and B are amino and carboxy side chain protecting groups, respectively, D is a carboxyl-activating mixed anhydride or active ester group)

The first of the reaction sequences illustrated above, to give the Asp-Pro-Arg intermediate, is begun by converting aspartic acid which has its amino and side chain carboxyl groups protected, e.g., as carbobenzoxy-$\beta$-benzyl-L-aspartic acid, to a carboxyl-activated derivative. A carboxyl-activated derivative can be obtained by forming the p-nitrophenyl ester, as illustrated, or a like ester, e.g., the hydroxysuccinimide ester, or by using a mixed anhydride such as ethyl chloroformate, isopropyl chloroformate, or the like. This reaction is carried out in a suitable organic solvent, e.g, a lower alkyl alkanoate such as ethyl acetate or a lower alkyl ketone such as methyl ethyl ketone or acetone, in the presence of a coupling agent such as DCC or the like, first at low temperature, e.g., from about $-5°$ C. to about $20°$ C., and preferably at about $5°$ C., for from about 30 minutes to about eight hours, and preferably for at least two hours, and then at a somewhat elevated temperature, e.g., from about $20°$ C. to about $30°$ C., for from about one to about eight hours, and preferably for at least three hours, to insure substantially complete conversion to the carboxyl-activated ester.

After removing any solid by-products formed, e.g., filtering off the dicyclohexylurea formed when DCC is used, the carboxyl-activated moiety is recovered by concentrating the reaction medium, preferably by vacuum concentration carried out, e.g., at from about 0.001 to about 550 mm/Hg, and preferably at about 15 mm/Hg, at a temperature preferably below about $60°$ C., followed by crystallization or precipitation of the thus-obtained thick oil or solid from a suitable solvent or solvent system, e.g., a lower alkanol, preferably one essentially unreactive with the activated carboxyl group, such as ethanol, n-propanol or isopropanol, alone or admixed with water or a lower alkanoic acid such as acetic acid, or lower alkyl alkanoate/hydrocarbon mixtures such as ethyl acetate/hexane, ethyl acetate/heptane, and the like.

Throughout the process of this invention the solvents, other additives and conditions used in purifying intermediates and final products are chosen, in every case, so as to give:

crystalline or amorphous solid products, and products of acceptable purity, i.e., ones having levels of impurities meeting FDA standards for peptide products, particularly in the final Asp-Ser-Asp-Pro-Arg.

B. Preparation of

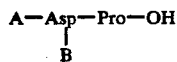

The carboxyl-activated ester is then coupled with proline. This reaction takes place in the absence of added coupling agent, and will preferably be carried to completion in a mixture of water and a lower alkyl formamide or acetamide, e.g., dimethylformamide/water, at a temperature preferably ranging from about $5°$ C. to about $30°$ C. at a slightly acidic, neutral or slightly alkaline pH, preferably a pH of about 7-8.

The desired compound is recovered from the reaction mixture by dilution with a suitable solvent, e.g., a lower alkanoate such as ethyl acetate. Depending on the mole ratios of the amino acids used in this step, the product can be recovered directly from the diluted reaction mixture by filtration or by extraction following acidification with a dilute aqueous solution of a strong acid. For acidification, mineral acids such as hydrochloric and sulfuric are preferred over strong organic acids, since mixtures containing the latter are more difficult to purify.

Again throughout the process of this invention, single amino acids being coupled to other protected amino acids or to peptide linkage-containing intermediates can be added in stoichiometric amounts or in excess of the stoichiometric amount (depending largely on the cost of the amino acid being coupled), e.g., in amounts ranging from about 0.5 to about 45 mole % above the stoichiometric amount, to help drive the coupling reaction to completion.

C. Preparation of

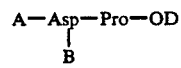

The thus-obtained Asp-Pro intermediate in which the carboxyl substituent on the Pro moiety is unprotected and thus available for reaction is then converted to a carboxyl-activated derivative. For example, the p-nitrophenyl ester can be obtained using the reaction conditions and recovery procedures described in Section I(A) above for the protected Asp p-nitrophenyl ester.

D. Preparation of

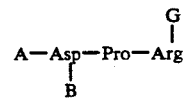

The resulting Asp-Pro carboxyl-activated derivative is coupled with arginine or an arginine side chain acid salt, e.g., the hydrofluoride, hydrochloride, hydrobromide or trifluoroacetate. The terminal amino group in the arginine side chain can also be protected, if desired, e.g., as the corresponding nitroarginine derivative, to improve the crystallinity of the coupled product and reduce side reactions during coupling. This reaction is carried to completion in a strongly polar solvent, such as dimethylformamide, dimethylacetamide, N-methylpyrrolidinone, dimethylsulfoxide, or the like, or in a mixture of one or more of such solvents admixed with water, preferably but not necessarily in the presence of a facilitating catalyst such as 1-hydroxybenzotriazole or the like, at a temperature preferably ranging from about $0°$ C. to about $30°$ C. at a slightly acidic, neutral or slightly alkaline pH, preferably a pH of about 7-8.

The solid product formed is collected by filtration and washed. The reaction solvent or a water/solvent mixture, e.g., a dimethylformamide/water mixture, can be used to wash the product, followed by distilled water. The washed product can then be dissolved in a suitable solvent or solvent system, e.g., a lower alkanoic acid such as acetic acid admixed with water, and the pH of the solution can be adjusted to about 3–7, preferably about 4.0 to about 4.5, using aqueous base such as sodium hydroxide or the like, to precipitate the product. The thus-obtained partially protected Asp-Pro-Arg is washed with water, acetone or the like and dried in a vacuum at a temperature below about 60° C., preferably about 15°–30° C.

E. Preparation of

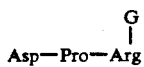

The partially protected Asp-Pro-Arg is deprotected in one step by removing the benzyloxycarbonyl, benzyl or nitro groups by catalytic hydrogenation. Any hydrogenation catalyst useful in hydrogenation reactions that reduce benzyloxycarbonyl, benzyl or nitrobonds, and preferably a palladium-containing catalyst such as palladium metal per se or palladium on a suitable support, e.g., carbon, can be used at hydrogen pressures ranging from below atmospheric to superatomospheric, e.g. a pressure of from about 1 to about 250 psig, and preferably about 50 psig. The partially protected Asp-Pro-Arg will preferably be dissolved in any solvent or solvent system with which it will not react, e.g., an aqueous lower alkanoic acid such as acetic acid, a lower alkanoic acid salt such as ammonium acetate, a lower alkanol such as ethanol, or the like. The course of the reaction, i.e., completeness of hydrogenation (deprotection), can readily be followed by thin layer chromatography of small samples taken from the reaction medium.

Upon completion of the reaction the catalyst is filtered off and the product precipitated from the filtrate by pouring it into a lower alkyl ketone such as acetone or methyl ethyl ketone or a lower alkanoate such as ethyl acetate. If an Asp-Pro-Arg acid salt is desired, an acid such as hydrochloric, hydrobromic, acetic or trifluoroacetic acid can be added.

II. PREPARATION OF ASP-SER-ASP-PRO-ARG

F. Preparation of

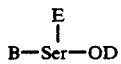

(E represents the hydroxyl-containing side chain of serine unprotected or bearing a hydroxyl protecting group)

The second of the reaction sequences illustrated above, using the Asp-Pro-Arg intermediate to produce Asp-Ser-Asp-Pro-Arg, is begun by converting serine which has both its hydroxyl and amino groups protected, e.g., as t-butyloxycarbonyl-O-benzyl-L-serine, or only its amino group protected, e.g., as t-butyloxycarbonyl-L-serine, to a carboxyl-activated derivative, e.g., the hydroxysuccinimide ester as illustrated, the p-nitrophenyl ester, or a like ester, again using essentially the same reaction conditions and recovery procedures described above for the Asp p-nitrophenyl ester. A lower alkanol, again preferably one essentially unreactive with the activated carboxyl group, such as ethanol, n-propanol or isopropanol, is preferably used as the crystallization or precipitation solvent. Water, or a lower alkanoic acid such as acetic acid, or mixtures thereof can be added as well to increase the yield of crystallized or precipitated carboxyl-activated ester.

G. Preparation of

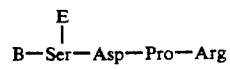

The carboxyl-activated ester is then coupled with unprotected Asp-Pro-Arg or an acid salt thereof, e.g., the hydrochloride salt. This reaction takes place without a coupling agent, and whether serine has both its hydroxyl and amino groups protected or only its amino group protected, will preferably be carried out in a mixture of water and a suitable water-miscible volatile organic solvent or solvents other than an alkanol, e.g., a lower alkyl ketone such as methyl ethyl ketone or acetone, at a temperature ranging from about −20° C. to about 50° C., and preferably from about 20° C. to about 30° C., at a slightly acidic, neutral or slightly alkaline pH.

The pH of the solution is then adjusted to the acidic side, e.g., to a pH of from about 2.5 to about 7, and preferably from about 4.0 to about 4.5, using an acid such as acetic acid, trifluoroacetic acid, hydrochloric acid, or the like, and the volatile organic solvent removed under vacuum. Care should be taken at this point, and indeed throughout the entire workup, to keep the temperature below about 40° C., and preferably at room temperature or below, e.g., at about 15° C., to avoid unwanted side reactions that can occur at higher temperatures due to the presence of unstable bonds, free amino acids etc.

A partitioning solvent or solvent mixture, e.g., a mixture of a lower alkanoic acid such as acetic acid with a lower alkanol such as n-butanol or a lower alkyl alkanoate such as ethyl acetate, is then added to concentrate the desired product in an upper organic phase and by-products, etc. in a lower aqueous phase. A salt such as sodium chloride, ammonium sulfate, ammonium acetate, or the like can also be added to facilitate clean separation of the desired product. After separating the lower, aqueous layer, the upper layer is washed with an aqueous salt solution, e.g., aqueous sodium chloride, and concentrated under vacuum at a temperature below about 40° C. The resulting residue is dissolved in a suitable organic solvent, e.g., a lower alkanol such as isopropanol or a lower alkanoate such as ethyl acetate, to which magnesium sulfate, sodium sulfate, or the like can be added to dry the solvent. The resulting slurry is then filtered, the filtrate is concentrated and washed with a lower alkyl alkanoate such as ethyl acetate, and the product is dried under vacuum, again at a temperature below about 40° C.

H. Preparation of

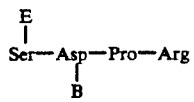

Next, the amino protected peptide is deprotected, for example by using hydrogen chloride or hydrogen bromide dissolved in a lower alkanoic acid such as acetic acid, alone or together with a lower alkyl alkanoate, e.g., an acetic acid/ethyl acetate mixture, or a cyclic ether such as dioxane or tetrahydrofuran, or the like, or by using trifluoracetic acid, preferably dissolved in a halogenated hydrocarbon solvent, e.g., chloroform or methylene chloride, at room temperature, ranging from about −50° C. to about 40° C., and preferably at room temperature, to give the corresponding deprotected hydrohalide, e.g., O-benzyl-L-seryl-L-aspartyl-L-prolyl-L-arginine hydrochloride as illustrated.

I. Preparation of

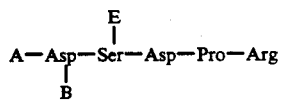

The thus-obtained hydrohalide is collected by filtration, washed, and then dissolved in a suitable solvent, e.g., a dialkylformamide or acetamide, such as dimethylformamide, or a ketone such as acetone, or mixtures thereof with water, such as a dimethylformamide/water mixture or an acetone/water mixture, and reacted with a carboxyl-activated aspartic acid derivative having its amino and side chain carboxyl groups protected, i.e., the product of the first step of the first of the reaction sequences illustrated above, such as carbobenzoxy-β-benzyl-L-aspartic acid p-nitrophenyl ester, which has also been dissolved in a suitable solvent, e.g., acetone, dimethylformamide, or the like, or mixtures thereof with water. An activating catalyst such as 1-hydroxybenzotriazole will preferably be present, and the coupling reaction will preferably be carried out at a temperature ranging from about 20° C. to about 30° C., preferably at a slightly acidic, neutral or slightly alkaline pH.

The volatile organic solvent is removed under vacuum. The product can then be worked up from that point on in the same manner as described in the previous step in the synthesis, care again being taken to keep the temperature below about 40° C., and preferably from about 15° C. to about 25° C. The product can also be crystallized using a suitable crystallization solvent, e.g., a ketone such as acetone a lower alkanol such as isopropanol, or mixtures thereof with water, a lower alkyl alkanoate such as ethyl acetate, or the like. Recrystallization of the product can also be carried out as described in step D of the first of the reaction sequences illustrated above.

J. Preparation of Asp-Ser-Asp-Pro-Arg

The intermediate diprotected (having an unprotected hydroxyl group in the hydroxyl-containing serine side chain) or triprotected pentapeptide is deprotected by catalytic hydrogenation as described in Step E of the first of the reaction sequences illustrated above.

In steps H and I of reaction sequence II as just described, the intermediate diprotected or triprotected pentapeptide product of step H may be recovered as the hydrohalide salt, e.g., the hydrochloride or hydrobromide, which is then subjected to catalytic dehydrogenation to remove its two or three protecting groups, thus giving Asp-Ser-Asp-Pro-Arg as the hydrohalide salt. If desired, the free base can then be obtained, or the hydrohalide salt converted to another suitable salt, e.g., the acetate salt, and if necessary impurities can be diminished by passing the Asp-Ser-Asp-Pro-Arg hydrohalide, dissolved in a suitable solvent, such as water or mixtures of water with a lower alkanoic acid such as acetic acid, or a lower alkyl alkanoate such as ethyl acetate, or a lower alkanol such as isopropanol, or the like, over an ion exchange resin such as Dowex 1X-2 in the acetate form, Amberlite IRA-400 in the acetate form, DEAE-Sephadex, or the like, at a temperature of from about 5° C. to about 40° C., and preferably from about 15° C. to about 30° C.

Other salts can be prepared in known manner simply by dissolving free base compound in a suitable solvent, adding the acid whose salt is desired, and then drying to give the salt.

Alternatively, the hydrohalide salt product of reaction sequence II, step C can be subjected, before hydrogenation, to a neutralization step to obtain the free base at this point in the synthesis. This can be accomplished by dissolving the hydrohalide salt in a suitable organic solvent, e.g., methanol, dimethylformamide, or the like, and neutralizing with a mild base, such as dilute sodium bicarbonate, potassium carbonate, or the like, at a temperature of from about 5° C. to about 40° C., and preferably from about 15° C. to about 30° C., and then extracting the neutralized product with an organic solvent, e.g., a lower alkanoate such as ethyl acetate, a lower alkanol such as n-butanol, or the like.

In order that those skilled in the art can more fully understand this invention, the following examples are set forth. These examples are given solely for purposes of illustration, and should not be considered as expressing limitations unless so set forth in the appended claims. All percentages are by weight, unless otherwise stated.

EXAMPLE I

Preparation of N-Carbobenzoxy-β-Benzyl-L-Aspartic Acid p-Nitrophenyl Ester

N-carbobenzoxy-β-benzyl-L-aspartic acid (12 Kg) and p-nitrophenol (5.1 Kg) are dissolved in ethyl acetate (20-30 L) and the solution is cooled to below 5° C. Dicyclohexyl-carbodiimide (7.6 Kg) is dissolved in ethyl acetate (8-12 L) and added, maintaining the temperature below 5° C. The solution is stirred at reduced temperature for two hours and then for three hours at 20°-30° C. The dicyclohexylurea byproduct is removed by filtration and washed with ethyl acetate (20-30 L). The filtrate is concentrated in vacuo below 60° C. The concentrate is dissolved in a mixture of hot isopropyl alcohol (25-40 L) and distilled water (2-5 L) and cooled below 25° C. The solids are collected on a filter, rinsed with isopropyl alcohol and dried below 40° C. Melting point=76°-79° C.; specific rotation=−15° to 18° (C=1, DMF).

EXAMPLE II

Preparation of N-Carbobenzoxy-β-Benzyl-L-Aspartyl-L-Proline

L-Proline (2.8 Kg) and N-carbobenzoxy-β-benzyl-L-aspartic acid p-nitrophenyl ester (10.5 Kg) are dissolved in a mixture of dimethylformamide (25-30 L) and distilled water (9-13 L). The pH of the solution is adjusted to 7.5-8.0 and maintained in this range by addition of diisopropylethylamine. The mixture is stirred at 20°-30° C. until the reaction is complete. The solution is diluted with ethyl acetate (45-55 L) and extracted with dilute hydrochloric acid (15-20 L). The aqueous layer is back extracted with ethyl acetate (8-12 L). The combined organic layers are washed three times with dilute hydrochloric acid (10-15 L). The organic layer is extracted with dilute sodium bicarbonate. Ethyl acetate (40-60 L) is added to the aqueous layer and the pH is adjusted to about 3.0 by addition of dilute hydrochloric acid. The organic layer is washed two times with dilute hydrochloric acid (10–30 L) and concentrated in vacuo below 55° C. to 20–30 L.

EXAMPLE III

Preparation of N-Carbobenzoxy-β-Benzyl-L-Aspartyl-L-Proline p-Nitrophenyl Ester p-Nitrophenol (3.0 Kg) is added to the concentrated ethyl acetate solution of N-carbobenzoxy-β-benzyl-L-aspartyl-L-proline prepared as described in Example II above. The solution is cooled below 5° C. Dicyclohexylcarbodiimide (4.5 Kg) is dissolved in ethyl acetate (10–20 L) and added, maintaining the temperature below 5° C. The solution is stirred at reduced temperature for two hours and then for three hours at 20°–30° C. The dicyclohexylurea is removed by filtration and washed with ethyl acetate (20–30 L). The filtrate is concentrated in vacuo below 60° C. The concentrate is dissolved in hot isopropyl alcohol (50–70 L) and cooled below 25° C. The solids are collected on a filter, rinsed with isopropyl alcohol and dried below 40° C. Melting point=88°–91° C.; specific rotation= −70° to −73° (C=1, ethyl acetate).

EXAMPLE IV

Preparation of N-Carbobenzoxy-O-Benzyl-L-Aspartyl-L-Prolyl-L-Arginine

Arginine hydrochloride (2.3 Kg) and 1-hydroxybenzotriazole hydrate (1.5 Kg) are dissolved in a mixture of distilled water (5–6 L) and dimethylformamide (10–12 L). The pH of the solution is adjusted to 7.0–7.5 by addition of diisopropylethylamine. N-carbobenzoxy-β-benzyl-L-aspartyl-L-proline p-nitrophenyl ester (5.8 Kg) is dissolved in dimethylformamide (5–10 L) and added, maintaining the pH of solution at 7.0–7.5 with diisopropylethylamine. The solution is stirred at 20°–30° C. until the pH remains constant. The solids are collected on a filter, rinsed with a mixture of dimethylformamide (20–25 L) and distilled water (20–25 L), followed by distilled water 20–30 L). The product is dissolved in acetic acid (12–15 L) and the solution is diluted with distilled water (50–60 L). The pH is adjusted to 4.0–4.5 by addition of dilute sodium hydroxide. The solids are collected on a filter and washed with distilled water followed by acetone and then dried below 60° C.

EXAMPLE V

Preparation of L-Aspartyl-L-Prolyl-L-Arginine

N-Carbobenzoxy-β-benzyl-L-aspartyl-L-prolyl-L-arginine (4.2 Kg) is dissolved in acetic acid (20–30 L and distilled water (15–20 L). Palladium on charcoal (0.5 Kg) is added and the mixture is purged with nitrogen and then contacted with hydrogen flowing at a rate of 50–200 L/hr for three to sixteen hours at 15°–30° and from atmospheric pressure to 50 psig Completeness of hydrogenation is checked by thin layer chromatography, and hydrogenation is continued, if necessary, to substantial completion:
Plates: Silica gel
Mobile Phase: Chloroform - methanol - Acetic acid - Water (36:27:4:8)
Detection: Short wave UV light; chlorine followed by a spray of 1% O-tolidine Once the hydrogenation reaction is complete the catalyst is removed by filtration and rinsed with distilled water (5–15 L). The filtrate is then poured into acetone. The resultant solids are collected on a filter, rinsed with acetone and dried below 60° C.

EXAMPLE VI

Preparation of t-Butyloxycarbonyl-O-Benzyl-L-Serine Hydroxysuccinimide Ester t-Butyloxycarbonyl-O-benzyl-L-serine (3 Kg) and N-hydroxysuccinimide (1.3 Kg) are dissolved in ethyl acetate (10–15 L) and the solution is cooled to below 5° C. Dicyclohexylcarbodiimide (2.3 Kg) is dissolved in ethyl acetate (4–6 L) and added, maintaining the temperature below 5° C. The solution is stirred at reduced temperature for two hours and then for three hours at 20°–30° C. The dicyclohexylurea is removed by filtration and washed with ethyl acetate. The filtrate is concentrated in vacuo below 60° C. The concentrate is dissolved in hot isopropyl alcohol (10–20 L) and cooled below 25° C. The solids are collected on a filter, rinsed with isopropyl alcohol and dried below 40° C. Melting point=111°–114° C.; specific rotation=5° to 6° (C=1, dioxane).

EXAMPLE VII

Preparation of t-Butyloxycarbonyl-O-Benzyl-L-Seryl-L-Aspartyl-L-Prolyl-L-Arginine L-Aspartyl-L-prolyl-L-arginine prepared as described in Example V above (2.7 Kg), is dissolved in distilled water (5–7 L). The pH of the solution is adjusted to 7.0–7.5 and maintained at that value by the addition of diisopropyl-ethylamine. t-Butyloxycarbonyl-O-benzyl-L-serine hydroxy-succiniimide ester (2.8 Kg) is dissolved in acetone and this solution is added to the previous solution. The solution is stirred until the pH remains constant. The pH is then adjusted to 4.0–4.5 with acetic acid and the solution is concentrated in vacuo. The residue is dissolved in isopropyl alcohol. Magnesium sulfate (50–100 g/L) is added and the slurry is filtered. The filtrate is concentrated and poured into ethyl acetate. The product is dried in vacuo below 40° C.

EXAMPLE VIII

Preparation of O-Benzyl-L-Seryl-L-Aspartyl-L-Prolyl-L-Arginine Hydrochloride t-Butyloxycarbonyl-O-L-seryl-L-aspartyl-L-prolyl-L-arginine (4.0 Kg) is dissolved in a solution of hydrogen chloride (3.0–5.0 Kg) in acetic acid (70–80 L). The solution is stirred for 30 minutes and then concentrated in vacuo. The concentrate is dissolved in isopropyl alcohol (20–30 L) and poured into ethyl acetate (130–200 L). The resultant solids are collected by filtration, washed with ethyl acetate and dried below 40° C.

EXAMPLE IX

Preparation of N-Carbobenzoxy-O-Benzyl-L-Aspartyl-O-Benzyl-L-Seryl-L-Aspartyl-L-Prolyl-L-Arginine O-Benzyl-L-seryl-L-aspartyl-L-prolyl-L-arginine hydrochloride (3.0 Kg) and 1-hydroxybenzotriazole (1.0

Kg) are dissolved in a mixture of distilled water (4.8 L) and acetone (10–15 L). The pH of the solution is adjusted to 7.0–7.5 with diisopropylethylamine. N-Carbobenzoxy-β-benzyl-L-aspartic acid p-nitrophenyl ester (2.2 Kg) is dissolved in acetone (5–10 L) and added while maintaining the pH of the solution at 7.0–7.5 with diisopropylethylamine. The solution is stirred at 20°–30° C. until the pH remains constant.

Following pH stabilization the acetone is removed in vacuo and ethyl acetate and saturated sodium chloride solution are added to the residue. A sufficient amount of isopropyl alcohol is added to form two layers.

The upper layer is washed several times with an aqueous sodium chloride solution and then concentrated in vacuo to an oil or a solid. This residue is dissolved in acetone (10–20 L) and, after stirring, the resulting crystalline precipitate is collected on a filter, washed with acetone, distilled water and acetone again, and then dried in vacuo below 45° C. Melting point = 140°–144° C.; specific rotation = 44° to −48° (C−1, acetic acid).

EXAMPLE X

Preparation of
L-Aspartyl-L-Seryl-L-Aspartyl-L-Prolyl-L-Arginine

N-carbobenzoxy-O-benzyl-L-aspartyl-O-benzyl-L-seryl-L-aspartyl-L-prolyl-L-arginine (2.7 Kg) is dissolved in 19 L of aqueous 2.3M ammonium acetate. Palladium on charcoal (5–20%) is added. The mixture is purged with nitrogen and then contacted with hydrogen flowing at a rate of 50–100 L/hr for three to sixteen hours at 15°–25° C. and from atmospheric pressure to 50 psig.

Completeness of hydrogenation is checked by thin layer chromatography, and hydrogenation is continued, if necessary, to substantial completion:
PATENT
Plates: Silica gel
Mobile Phase: Chloroform-methanol-acetic acid-water (36:27:4:8),
Detection: Short wave UV light; chlorine followed by a spray of 1% O-tolidine.

The catalyst is removed by filtration and rinsed with aqueous acetic acid or ammonium acetate. The filtrate and washings are concentrated to about 7 L and the concentrate poured into ethanol (70 L) and the resultant solids collected by filtration, washed with ethanol and dried in vacuo below 50° C. The product is dissolved in distilled water and charged to a column of Dowex 1×2 resin (acetate form). The resin bed is washed with distilled water (50–100 L) and eluted with 5% ammonium acetate in distilled water (100–200 L). Product fractions are pooled, concentrated and poured into ethanol, (70 L). The resulting product is dissolved in distilled water and concentrated to remove the ethanol. The solution is frozen and then lyophilized.

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

We claim:

1. A method of synthesizing L-aspartyl-L-seryl-L-aspartyl-L-prolyl-L-arginine which comprises the steps of:

A. converting L-aspartic acid having a protected amino group and a protected side chain carboxyl group to a carboxyl-activated derivative thereof;

B. reacting the carboxyl-activated L-aspartic acid derivative with L-proline to give an L-aspartyl-L-proline intermediate whose L-aspartyl moiety has its amino group and side chain carboxyl group protected;

C. converting the L-aspartyl-L-proline intermediate to a carboxyl-activated derivative thereof whose L-aspartyl moiety has its amino group and side chain carboxyl group protected;

D. reacting the carboxyl-activated L-aspartyl-L-proline intermediate with L-arginine, L-nitroarginine, or an L-arginine side chain acid salt to give an L-aspartyl-L-prolyl-L-arginine intermediate whose L-aspartyl moiety has its amino group and side chain carboxyl group protected and whose L-arginine moiety has its terminal amino group unprotected or protected as the nitroarginine derivative;

E. deprotecting the L-aspartyl-L-prolyl-L-arginine intermediate to give L-aspartyl-L-prolyl-L-arginine;

F. converting L-serine having a protected amino group and an unprotected or protected side chain hydroxyl group to a carboxyl-activated derivative thereof;

G. reacting the carboxyl-activated L-serine derivative with L-aspartyl-L-prolyl-L-arginine to give an L-seryl-L-aspartyl-L-prolyl-L-arginine intermediate whose L-seryl moiety has its amino group protected and side chain hydroxyl group protected or unprotected;

H. deprotecting the amino group in the L-seryl moiety of the L-seryl-L-aspartyl-L-prolyl-L-arginine intermediate;

I. reacting the deprotected amino group-containing L-seryl-L-aspartyl-L-prolyl-L-arginine with a carboxyl-activated derivative of L-aspartic acid, the L-aspartic acid having a protected amino group and a protected side chain carboxyl group, to give an L-aspartyl-L-seryl-L-aspartyl-L-prolyl-L-arginine intermediate whose terminal L-aspartyl moiety has its amino group and side chain carboxyl group protected and whose L-seryl moiety has its side chain hydroxyl group protected or unprotected;

J. deprotecting the L-aspartyl-L-seryl-L-aspartyl-L-prolyl-L-arginine intermediate to give L-aspartyl-L-seryl-L-aspartyl-L-prolyl-L-arginine.

2. A method as recited in claim 1 carried out using L-nitroarginine.

3. A method as recited in claim 1 carried out using L-serine having a protected amino group and an unprotected side chain hydroxyl group.

4. A method which comprises reacting an L-seryl-L-aspartyl-L-prolyl-L-arginine, whose L-seryl moiety has its side chain hydroxyl group protected, with a carboxyl-activated L-aspartic acid derivative having a protected amino group and a protected side chain carboxyl group to give L-aspartyl-L-seryl-L-aspartyl-L-prolyl-L-arginine whose terminal L-aspartyl moiety has its amino group and its side chain carboxyl group protected and whose L-seryl group has its side chain hydroxyl group protected.

5. A method which comprises reacting O-benzyl-L-seryl-L-aspartyl-L-prolyl-L-arginine hydrochloride with N-carbobenzoxy-β-benzyl-L-aspartic acid p- nitrophenyl ester to give N-carbobenzoxy-O-benzyl-L-aspartyl-O-benzyl-L-seryl-L-aspartyl-L-prolyl-L-arginine.

6. A method which comprises reacting L-seryl-L-aspartyl-L-prolyl-L-arginine with a carboxyl-activated L-aspartic acid derivative having a protected amino group and a protected side chain carboxyl group to give L-aspartyl-L-seryl-L-aspartyl-L-prolyl-L-arginine whose terminal L-aspartyl moiety has its amino group and its side chain carboxyl group protected.

7. A method which comprises reacting L-seryl-L-aspartyl-L-prolyl-L-arginine hydrochloride with N-carbobenzoxy-β-benzyl-L-aspartic acid p-nitrophenyl ester to give N-carbobenzoxy-O-benzyl-L-aspartyl-L-seryl-L-aspartyl-L-prolyl-L-arginine.

8. The method of any one of claims 2, 3, 4, 5, 6 or 7 carried out at a temperature less than about 30° C. and a slightly acidic, neutral or slightly alkaline pH.

9. A method as recited in claim 8 in which the temperature ranges from about −5° C. to about 30° C. and the pH ranges from slightly above 7 to about 8.

10. A method as recited in claim 1 in which the L-aspartyl-L-prolyl-L-arginine intermediate whose L-aspartyl moiety has its amino group and side chain carboxyl group protected and whose L-arginine moiety has its terminal amino group unprotected or protected as the nitroarginine derivative is deprotected by catalytic hydrogenation.

11. A method as recited in claim 1 in which the L-aspartyl-L-seryl-L-aspartyl-L-prolyl-L-arginine intermediate whose terminal L-aspartyl moiety has its amino group and side chain carboxyl group protected and whose L-seryl moiety has its side chain hydroxyl group protected or unprotected is deprotected by catalytic hydrogenation.

* * * * *